United States Patent [19]

Testerman

[11] 4,341,221
[45] Jul. 27, 1982

[54] SHIELDED RECORDING ELECTRODE SYSTEM

[75] Inventor: Roy L. Testerman, New Hope, Minn.

[73] Assignee: Medtronic, Inc., Minneapolis, Minn.

[21] Appl. No.: 195,169

[22] Filed: Oct. 7, 1980

[51] Int. Cl.³ .............................................. A61B 5/04
[52] U.S. Cl. .................................................... 128/642
[58] Field of Search .............. 128/642, 639, 640, 644, 128/784, 785, 419 C

[56] References Cited

U.S. PATENT DOCUMENTS

| Re. 26,810 | 3/1970 | Schwartz et al. | 128/784 |
|---|---|---|---|
| 3,654,933 | 4/1972 | Hagfors | 128/784 |
| 3,738,368 | 6/1973 | Avery et al. | 128/418 |
| 3,774,618 | 11/1973 | Avery | 128/418 |
| 3,957,036 | 5/1976 | Normann | 128/642 |
| 3,994,302 | 11/1976 | Brennen | 128/784 |
| 4,046,141 | 9/1977 | DeLuca | 128/642 |
| 4,122,843 | 10/1978 | Zdrojkowski | 128/644 |
| 4,308,868 | 1/1982 | Jhabvala | 128/421 |

OTHER PUBLICATIONS

Banzett, "Implantable Electrode Pair . . . ", IEEE Trans. on Bio. Med. Eng., vol. 27, No. 1, Jan. 1980, pp. 53-54.
DeLaunois, "Easy Recording . . . Potentials", Med. & Bio. Eng. & Comp., Mar. 1973, 16, No. 2, pp. 219-220.
Stein, R. B. & Pearson, K. G. "Predicted Amplitude & Form of Action Potentials Recorded from Unmyelinated Nerve Fibres," Jan. 15, 1971.
Schad, H. & Seller, H. "A Method for Recording Autonomic Nerve Activity in Unanesthetized, Freely Moving Cats," Sep. 4, 1975.
Ninomiya, Ishio; Yonezawa, Yoshiharu & Wilson, Michael F., "Implantable Electrode for Recording Nerve Signals in Awake Animals" Jul. 1976.
Testerman, Roy L.; Hagfors, Norman R. & Schwartz, Seymour I., "Design and Evaluation of Nerve Stimulating Electrodes" Jan. 1971.

*Primary Examiner*—Lee S. Cohen
*Attorney, Agent, or Firm*—John L. Rooney; Joseph F. Breimayer; Carl A. Forest

[57] ABSTRACT

An electrode system for recording neural signals suitable for chronic implantation employing shielding and other techniques to improve signal-to-noise ratio. Three electrically isolated electrodes are used in a tripolar fashion. The electrodes are thin wires which are coated with a conductive gel. Each electrode is wrapped around the nerve trunk and held in place by a dielectric encapsulant. A shielding flap is wrapped about the assembly. The electrodes are coupled to conductors that travel through a shielded tube to the sensing electronics. The shield of the tube is electrically coupled to the shielding flap.

14 Claims, 5 Drawing Figures

SHIELDED RECORDING ELECTRODE SYSTEM

BACKGROUND OF THE INVENTION

1. Field of the Invention

The present invention relates generally to implantable medical electronic devices and more specifically relates to an electrode structure for recording of neural signals.

2. Description of the Prior Art

Electrical coupling of electrodes to neural tissue has been known for some time. The structure taught in U.S. Pat. Nos. 3,421,511 and 3,654,933 issued to Schwartz, et al and Hagfors, respectively, and assigned to the assignee of the present invention, are intended for chronic implantation to accomplish neural stimulation rather than neural sensing or recording. Therefore, these electrode configurations are optimized for stimulation and shielding is not employed for improvement of signal-to-noise ratio.

Stein and Pearson teach the desirability of reduced cuff diameter for neural sensing in *Journal of Theoretical Biology*, Vol. 32 (1971) at pages 539–558. The minimization of cuff diameter is limited, however, because of the damage caused by "pinching" the neural tissue. Similarly, damage results from wrapping wires around nerves as taught by Schad and Seller in *Brain Research*, Volume 100 (1975), at pages 425–430. In an attempt to overcome this problem, Ninomiya, et al, in *Journal of Applied Physiology*, Volume 41 (1976) at pages 111–114 teach the making of electrodes from soft cow skin. This approach, however, creates the risk of an immune reaction and is susceptible to electromagnetic interference as reported in the cited article.

An effective electrode arrangement is the tripolar configuration as taught by Testerman, et al, in *Medical Research Engineering*, Volume 10 (1971) at pages 6–11. See also Stein, et al, in *Brain Research*, Volume 128 (1977), at pages 21–38. Whereas the tripolar arrangement enhances signal-to-noise ratio, it does not provide for a traumatic minimal cuff diameter nor optimal rejection of electromagnetic interference.

SUMMARY OF THE INVENTION

The preferred embodiment of the present invention uses three electrodes in a tripolar configuration which are wrapped around the neural tissue. Minimal cuff diameter is achieved without trauma by encasing the metal wires of the electrodes in a soft conducting gel. The three electrodes are held in place by a rapidly curing dielectric encapsulant. A flap is wrapped about the three electrodes. By providing the flap with a conductive layer, the flap acts as a shield from electromagnetic interference. The conductive layer of the flap may be coupled to ground potential.

DETAILED DESCRIPTION OF THE PREFERRED EMBODIMENT

The preferred mode of the present embodiment is described herein as a tripolar electrode configuration for sensing neural activity. Those of ordinary skill in the art will be able to apply these teachings to other related uses.

Figure 1:
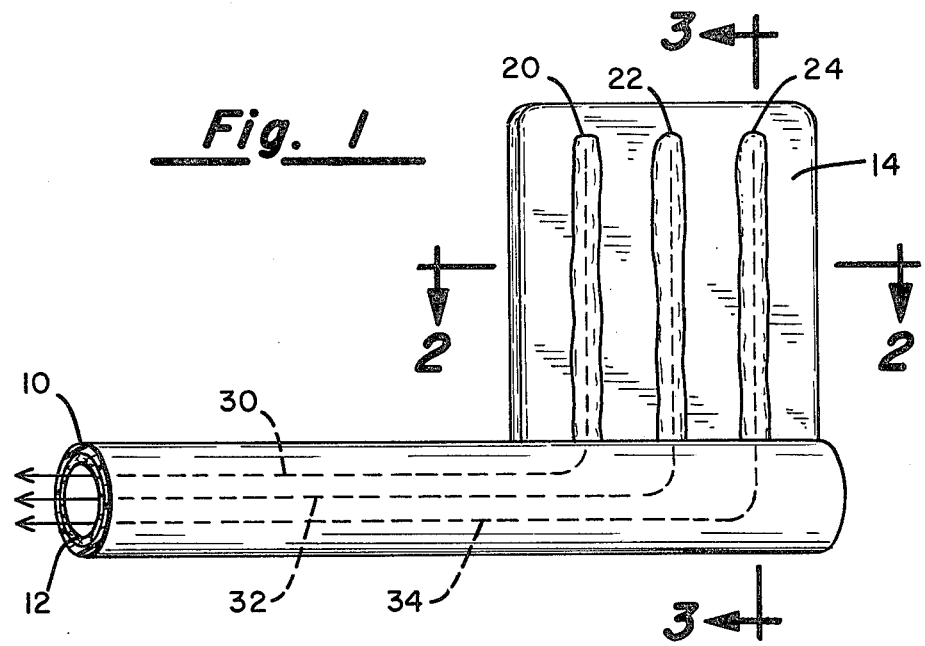
FIG. 1 is a plan view of electrode assembly employing the present invention prior to implantation.

FIG. 1 is a plan view of the electrode assembly. Tube 10 is an insulator such as silicon rubber which is substantially inert to body fluids. Located coaxially within tube 10 is shield 12 being of a conducting material suitable for shielding conductors 30, 32 and 34 from electromagnetic interference. Shield 12 may be connected to a grounding point at the proximal end (not shown) of tube 10. Conductors 30, 32 and 34 are mutually insulated conductors of low resistance. Conductors 30, 32 and 34 may be twisted or braided to provide additional noise immunity.

Flap 14 is attached to the underside of tube 10 as explained below. Flap 14 projects orthogonally from tube 10 as shown. Conductors 30, 32 and 34 exit tube 10 as shown and proceed in the direction of flap 14. Conductors 30, 32 and 34 are coated with an electrically conductive polymer such as NEURO ICE ™, available from the assignee of the present invention. The resulting tripolar structure has electrodes 20, 22 and 24 which are sufficiently soft to prevent trauma upon being wrapped about the nerve.

Figure 2:
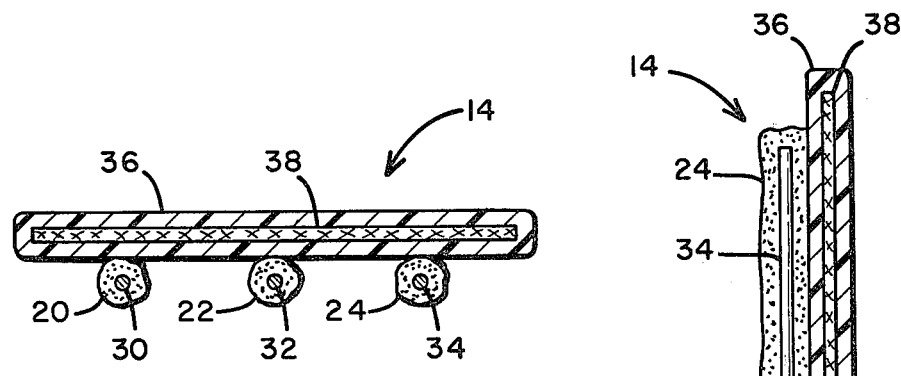
FIG. 2 is a sectional view of the flap of the electrode assembly.

FIG. 2 is an end sectional view of flap 14. Conducting shielding material 38 is shown as sandwiched within dielectric material 36. The substance used for dielectric material 36 is preferably the same as for tube 10 (e.g., silicon rubber). Conducting shielding material 38 may be of the same material as shield 12. Electrodes 20, 22 and 24 are shown as containing conductors 30, 32 and 34 of thin platinum/iridium wire or other suitable material covered with the conductive polymer gel. Electrodes 20, 22 and 24 merely rest on the surface of flap 14 but are not fixedly attached thereto.

Figure 3:
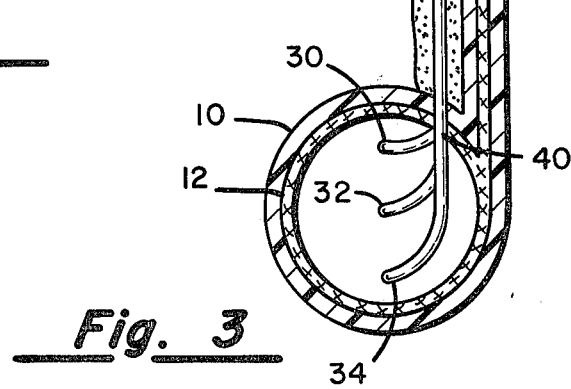
FIG. 3 is an end sectional view of the electrode assembly.

FIG. 3 is an end sectional view of tube 10. Shield 12 is directly connected to conducting shielding material 38. Preferably, conducting shielding material 38 is merely an extension of shield 12. Dielectric material 36 is shown in the preferred configuration wherein it is simply an extension of the main body of tube 10. Electrode 24 is shown as resting upon dielectric material 36. Conductor 34 is shown with bend at point 40. Conductors 30 and 32 may not be seen in this view but must be insulated to prevent interelectrode and electrode to shield electrical coupling.

Figure 4:
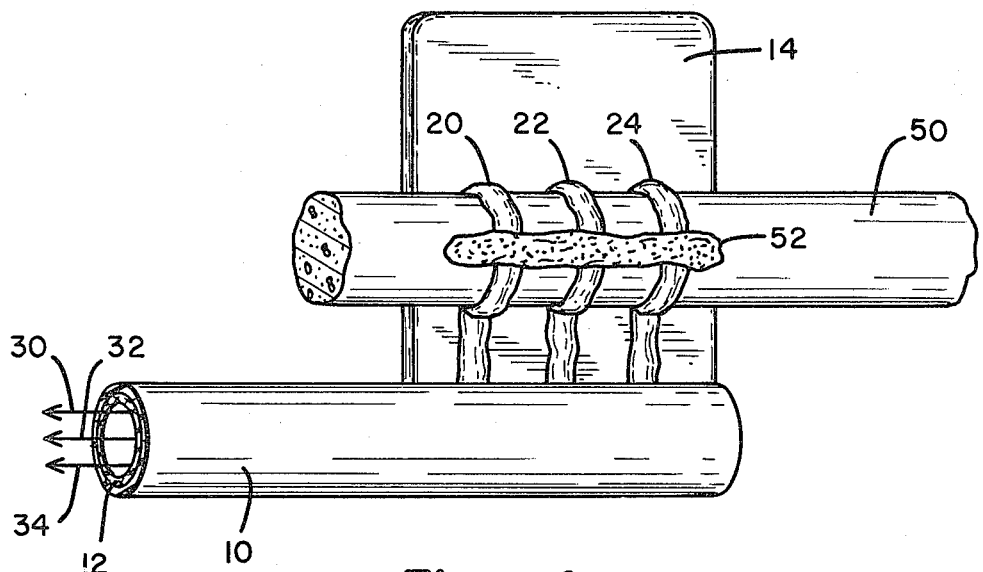
FIG. 4 is a view showing affixation of the electrodes.

FIG. 4 shows the electrode assembly during implantation. Tube 10 is held parallel to the nerve 50. Electrodes 20, 22 and 24 are wrapped about nerve 50. The interelectrode spacing may be readily adjusted. The electrodes (i.e., electrodes 20, 22 and 24) are wrapped sufficiently tightly around nerve 50 so that contact is made around the entire circumference. The conductive polymer gel provides electrical contact but is soft enough to prevent trauma. When electrodes 20, 22 and 24 are in the desired position, rapidly curing encapsulant 52 is applied to fixedly attach electrodes 20, 22 and 24 to nerve 50. A common medical adhesive may be used for encapsulant 52 which must be a dielectric.

Figure 5:
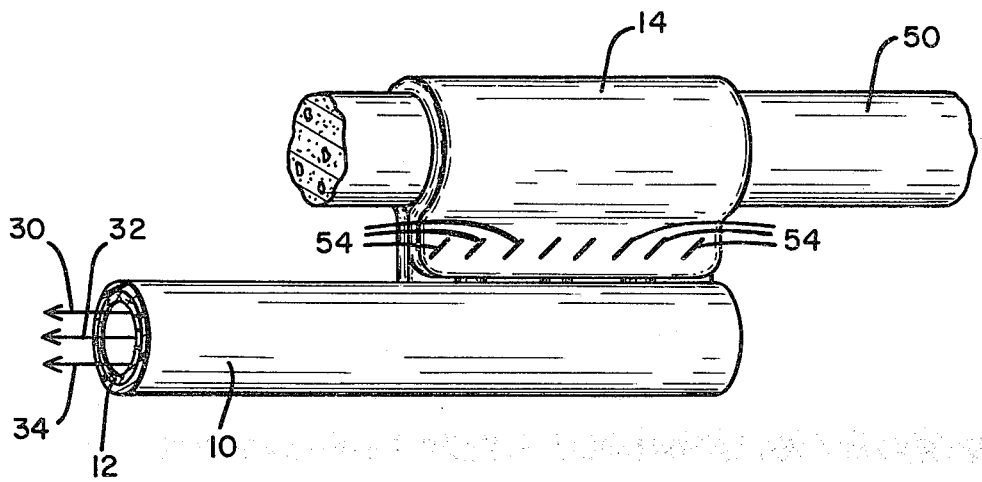
FIG. 5 shows the electrode assembly after completion of implantation.

FIG. 5 shows the completed assemblage. After encapsulant 52 has cured, flap 14 is wrapped around electrodes 20, 22 and 24. Completely enclosing and electrically shielding the electrodes, flap 14 may be closed upon itself and held with a medical adhesive or may be held using sutures 54 as shown.

Those skilled in the art will be able to apply these teachings to electrode systems using different materials and using different numbers and spacing of electrodes.

What is claimed is:

1. A method of detecting electrical activity of a nerve comprising:
   wrapping at least one electrode tightly about said nerve;
   shielding said at least one electrode from electromagnetic interference by wrapping a flap having a conductive shield about said at least one electrode; and
   electrically coupling at least one electrical conductor to said at least one electrode whereby said electrical activity of said nerve may be detected from said at least one electrical conductor.

2. A method according to claim 1 wherein said at least one electrode is three electrodes in a tripolar configuration and wherein said at least one electrical conductor is three mutually insulated electrical conductors each coupled to a different one of said three electrodes.

3. A method according to claim 1 or claim 2 further comprising:
   attaching said at least one electrode to said nerve with an encapsulant after said wrapping step but prior to said shielding step.

4. A method according to claim 3 wherein said conductive shield is electrically insulated from said nerve and from said at least one electrode and from said at least one conductor.

5. A method of detecting electrical activity of a nerve comprising:
   coating at least one bendable electrode with conductive gel whereby said electrode may be wrapped tightly around said nerve without damaging said nerve;
   wrapping said at least one bendable electrode around said nerve;
   electrically coupling at least one electrical conductor to said at least one bendable electrode whereby said electrical activity of said nerve may be detected from said at least one electrical conductor; and
   wrapping said at least one electrode with a bendable flap.

6. A method according to claim 5 further comprising attaching said at least one electrode to said nerve with a dielectric encapsulant prior to wrapping said electrode with said bendable flap.

7. A method according to claim 5 or claim 6 wherein said bendable flap further comprises a conductive shield whereby said at least one bendable electrode is shielded from electromagnetic interference.

8. A method according to claim 7 wherein said conductive shield is electrically insulated from said nerve and from said at least one bendable electrode and from said at least one electrical conductor.

9. An electrode system for recording activity of a nerve comprising:
   at least one bendable electrode having an outer surface of conductive gel whereby said at least one electrode may be wound about said nerve;
   at least one conductor coupled to said at least one electrode;
   a tube having a lumen containing said at least one conductor; and
   a flap fixedly attached to said tube adjacent said electrode whereby said at least one electrode may be covered after said at least one electrode is wrapped about said nerve.

10. An electrode system according to claim 9 wherein said flap further comprises:
    a conductive shield for electromagnetically shielding said at least one electrode.

11. An electrode system according to claim 10 wherein said tube further comprises:
    shielding means for electromagnetically shielding said at least one conductor.

12. An electrode system according to claim 11 wherein said outer surface of conductive gel is an outer surface of conductive polymer gel.

13. An electrode system according to claim 9, 10, 11 or 12 wherein said at least one bendable electrode is three electrodes in a tripolar configuration and wherein said at least one conductor is three mutually insulated conductors each attached to a different one of said three electrodes.

14. An electrode system according to claim 10 wherein said conductive shield is electrically insulated from said nerve and from said at least one electrode and from said at least one conductor.

* * * * *